United States Patent [19]

Laso

[11] 4,317,814

[45] * Mar. 2, 1982

[54] PREPARATION AND METHOD FOR TREATING BURNS

[76] Inventor: Felipe Laso, Montecito 59, Mexico City DF, Mexico

[*] Notice: The portion of the term of this patent subsequent to Oct. 20, 1998, has been disclaimed.

[21] Appl. No.: 158,650

[22] Filed: Jun. 12, 1980

[51] Int. Cl.³ .................... A61K 33/40; A61K 33/22; A61K 33/20; A61K 31/175
[52] U.S. Cl. .................................. 424/130; 424/148; 424/149; 424/323
[58] Field of Search ....................... 424/148, 149, 130

[56] References Cited

U.S. PATENT DOCUMENTS 2,701,781  2/1955  de Guevara .................... 424/148
3,147,124  9/1964  Wentworth .................... 424/149 X

OTHER PUBLICATIONS

Merck Index, 9th Ed. (1976) Nos. 4319, 4691, 8416, 7438.

Primary Examiner—Frank Cacciapaglia, Jr.
Attorney, Agent, or Firm—Parmelee, Miller, Welsh & Kratz

[57] ABSTRACT

A preparation and method for the treatment of burn victims. The preparation comprises an aqueous mixture of a perborate stabilized aqueous solution of chlorine oxides and glycerine. The preparation is applied to the burn area as a wet compress and the area exposed to ambient air between such applications.

9 Claims, No Drawings

PREPARATION AND METHOD FOR TREATING BURNS

BACKGROUND OF THE INVENTION

1. Field of the Invention

The present invention involves the treatment of burns of the skin in humans and is more particularly directed toward preparations for treatment of such burns and methods for using these preparations.

2. Prior Art

The stabilization of aqueous solutions of chlorine dioxide by the use of perborates has been disclosed in U.S. Pat. No. 2,701,781, the contents of said patent being incorporated by reference herein. As disclosed in said patent, a stabilized solution of chlorine dioxide in water can be formed by the combination of an inorganic boron compound, such as sodium tetraborate, boric acid or sodium perborate, and chlorine dioxide in the presence of an excess of water. In the preparation of this solution, the chlorine dioxide may be added as a gas or formed in situ in the aqueous media by addition of chlorite and/or hypochlorite salts under acidic conditions. It is believed that the chlorine dioxide, in this solution, is held in the form of a labile complex with the boron compound, and the stabilized composition so formed is described in the aforementioned patent as an antiseptic having no irritative tendency.

Additional uses for such stabilized aqueous chlorine dioxide compositions have been disclosed, for example, in U.S. Pat. No. 3,147,124, where a stabilized aqueous chlorine dioxide solution is described as a useful germicide upon addition of the same in a cheese making process.

It has now been found that a preparation consisting, in part, of a perborate stabilized aqueous solution of chlorine oxides is useful in treating burns.

SUMMARY OF THE INVENTION

The present invention is a preparation and method for treating burns in humans. An aqueous mixture of a perborate stabilized aqueous solution of chlorine oxides and glycerine is topically applied to the burn area. Said perborate stabilized aqueous solution of chlorine oxides, such as chlorine dioxide, preferably contains between about 4-12 parts by weight of sodium or potassium perborate per liter of water. The perborate stabilized aqueous solution of chlorine oxides also preferably contains a peroxide, such as hydrogen peroxide, sodium peroxide or potassium peroxide, or a percarbonate, such as sodium percarbonate or potassium percarbonate. The aqueous mixture preferably contains about 4 percent by weight of the perborate stabilized aqueous solution of chlorine oxides and about 6 percent by weight glycerine, with the remainder of the mixture being water.

DETAILED DESCRIPTION

As described in U.S. Pat. No. 2,701,781, a perborate stabilized aqueous solution of chlorine dioxide can be produced in which the chlorine dioxide is apparently held in the form of a labile complex with the boron compound.

In the formation of the present mixture, an aqueous mixture for use in treating burns is formed by preferably adding to water:

1. 4 weight percent of a perborate stabilized aqueous solution of chlorine oxides, containing about 4-12 parts of sodium or potassium perborate per liter of water, and
2. 6 weight percent glycerine.

The term "mixture" is used herein to mean the composition containing the perborate stabilized chlorine oxide solution and the glycerine, although it is postulated that the perborate stabilized chlorine oxides may in some manner react with the glycerine.

The perborate stabilized aqueous solution used to form the mixture is formed by preparing an aqueous solution containing 4-12 parts by weight of sodium or potassium perborate, per liter of water, the solution prepared by adding chlorine dioxide as a gas or formed in situ in the aqueous media by addition of chlorite and/or hypochlorite salts under acidic conditions, i.e. at a pH of less than 7.0, preferably a pH of between 2.5-4.5. While chlorine dioxide is believed to be the oxide of chlorine present in the solution, other oxides of chlorine may be present. During the passage or formation of chlorine oxides in the aqueous solution, under acidic conditions, it is believed that chlorous and chloric acids are formed which react with the perborates and gradually forms a clear, transparent aqueous solution.

In addition to the sodium or potassium perborate, the aqueous solution preferably has added thereto a peroxide selected from hydrogen peroxide, sodium peroxide or potassium peroxide, or a percarbonate such as sodium percarbonate or potassium percarbonate. The amount of peroxide or percarbonate added should be between 1 to 20 parts per liter of water, preferably between about 8-15 parts per liter of water.

In order to enhance the palatability of the aqueous stabilized solution of chlorine oxides, where the perborate stabilized aqueous solution of chlorine oxides is orally administered, in addition to being used as a component of the mixture, urea is added in an amount of between 0.5 to 20 parts per liter of water with about 6-20 parts preferred.

The formation of the perborate stabilized aqueous solutions of chlorine oxides which form part of the mixture of the present invention is described in co-pending application Ser. No. 158,649 filed June 12, 1980, entitled "Method of Combating Amebiasis in Humans", by the present inventor, the contents of said application being incorporated by reference herein.

The aqueous solution of perborate stabilized chlorine oxides, as described in said copending application, are formed by adding to 1000 cc of water the following:

80-120 grams sodium chlorite
90-130 grams sodium hypochlorite (13% aqueous solution)
5-7.5 cc of 37.7% hydrochloric acid
2-4.5 cc of 98.15% sulfuric acid
4-12 grams of an inorganic perborate selected from the group consisting of sodium perborate and potassium perborate, and
8-15 grams of sodium peroxide or an equivalent amount of potassium peroxide, hydrogen peroxide, potassium percarbonate or sodium percarbonate.

The mixture of an aqueous solution of perborate stabilized chlorine oxides, glycerine and water may be applied to the burn area by means of a wet compress. This application should take place at least twice, morning and evening, and preferably three times a day, for periods of 10-15 minutes per application. During the intervals between such applications the burn areas should be exposed to ambient air.

In addition to the application of this preparation directly to the burn area, it is recommended that a perborate stabilized aqueous solution of chlorine oxides also be administered internally. It is preferred that this orally administered solution contain sodium or potassium perborate in the amount of 4–12 parts per liter of water, and that it should be administered orally as 3–10 drops taken 4 times per day. This orally administrable, ingestible solution is described in the above identified co-pending application incorporated herein.

A number of second and third degree burn cases have been treated according to the method of the present invention, and highly satisfactory results have been obtained. In many of these cases the use of this method resulted in an immediate subsidence of burn-related pain. Healing in these cases was also rapid and was characterized by an absence of infection and contraction. Burn scars were smooth and resembled normal tissue, thus eliminating the need for plastic surgery in certain cases.

I claim:

1. A method of treating burns on humans to alleviate pain resulting therefrom and reduce scar formation, comprising:
    applying to the burn area of said human a wet compress containing an aqueous mixture of glycerine, and a perborate stabilized aqueous solution of chlorine oxides formed by adding to 1000 cc of water the following:
    80–120 grams sodium chlorite
    90–130 grams sodium hypochlorite (13% aqueous solution)
    5–7.5 cc of 37.7% hydrochloric acid
    2–4.5 cc of 98.15% sulfuric acid
    4–12 grams of an inorganic perborate selected from the group consisting of sodium perborate and potassium perborate, and
    8–15 grams of sodium peroxide or an equivalent amount of potassium peroxide, hydrogen peroxide, potassium percarbonate or sodium percarbonate.

2. The method of claim 1 wherein said glycerine is in an amount of about 6 percent by weight of the aqueous mixture.

3. The method of claim 1 wherein said aqueous mixture contains about 4 percent by weight of a perborate stabilized aqueous solution of chlorine oxides, 6 percent by weight glycerine, and the remainder is water.

4. The method of claim 1 wherein said wet compress is applied to said burn area for a period of about 10–15 minutes at least twice a day, and the burn area exposed to ambient air during the intervals between said applications.

5. The method of claim 1 wherein, in addition to applying said aqueous mixture to the burn area, an orally administrable perborate stabilized aqueous solution of chlorine oxides is orally administered, said orally administrable solution formed by adding to 1000 cc of water the following:
    80–120 grams sodium chlorite
    90–130 grams sodium hypochlorite (13% aqueous solution)
    5–7.5 cc of 37.7% hydrochloric acid
    2–4.5 cc of 98.17% sulfuric acid
    4–12 grams of an inorganic perborate selected from the group consisting of sodium perborate and potassium perborate, and
    8–15 grams of sodium peroxide or an equivalent amount of potassium peroxide, hydrogen peroxide, potassium percarbonate, or sodium percarbonate.

6. The method of claim 5 wherein said orally administrable perborate stabilized aqueous solution of chlorine oxides is administered 4 times per day in the amount of 3–10 drops per administration.

7. A preparation for treating burns on humans comprising an aqueous mixture of glycerine, and a perborate stabilized aqueous solution of chlorine oxides formed by adding to 1000 cc of water the following:
    80–120 grams sodium chlorite
    90–130 grams sodium hypochlorite (13% aqueous solution)
    5–7.5 cc of 37.7% hydrochloric acid
    2–4.5 cc of 98.15% sulfuric acid
    4–12 grams of an inorganic perborate selected from the group consisting of sodium perborate and potassium perborate, and 8–15 grams of sodium peroxide or an equivalent amount of potassium peroxide, hydrogen peroxide, potassium percarbonate or sodium percarbonate.

8. The preparation defined in claim 7 wherein said glycerine is present in an amount of about 6 percent by weight of the aqueous mixture.

9. The preparation defined in claim 7 wherein said perborate stabilized aqueous solution of chlorine oxides is present in an amount of 4 percent by weight of said aqueous mixture, said glycerine is present in an amount of about 6 percent by weight of said aqueous mixture, and the remainder is water.

* * * * *